(12) United States Patent
Iaconi-Forrer et al.

(10) Patent No.: US 7,857,129 B2
(45) Date of Patent: Dec. 28, 2010

(54) CONTAINER AND CARRIER SYSTEM FOR SURGICAL AUXILIARY MATERIAL

(75) Inventors: Ruth Iaconi-Forrer, Moehlin (CH); Andre Furrer, Lueterkofen (CH); Karina Candrian, Zuerich (CH)

(73) Assignee: Synthes USA, LLC, West Chester, PA (US)

( * ) Notice: Subject to any disclaimer, the term of this patent is extended or adjusted under 35 U.S.C. 154(b) by 387 days.

(21) Appl. No.: 10/591,547

(22) PCT Filed: Jun. 9, 2004

(86) PCT No.: PCT/IB2004/001882

§ 371 (c)(1),
(2), (4) Date: Jul. 6, 2007

(87) PCT Pub. No.: WO2005/092231

PCT Pub. Date: Oct. 6, 2005

(65) Prior Publication Data

US 2008/0302688 A1  Dec. 11, 2008

(30) Foreign Application Priority Data

Mar. 7, 2004  (CH) .................................. 00393/04

(51) Int. Cl.
 *B65D 85/24* (2006.01)
 *A47F 7/00* (2006.01)
 *A61L 2/00* (2006.01)
(52) U.S. Cl. ...................... 206/339; 206/370; 206/438; 211/85.13; 422/297
(58) Field of Classification Search ......... 206/336–347, 206/368, 370, 438, 557–565, 369, 63.3, 63.5; 211/85.13; 422/300, 297
See application file for complete search history.

(56) References Cited

U.S. PATENT DOCUMENTS

| | | | | |
|---|---|---|---|---|
| 3,624,867 A | * | 12/1971 | Reynolds | 206/345 |
| 5,046,611 A | * | 9/1991 | Oh | 206/339 |
| 5,279,416 A | * | 1/1994 | Malec et al. | 206/339 |
| 5,490,975 A | * | 2/1996 | Dane | 206/438 |
| 5,551,214 A | * | 9/1996 | Vincze et al. | 53/443 |
| 5,881,878 A | * | 3/1999 | Faccioli et al. | 206/438 |
| 5,967,318 A | * | 10/1999 | Rosler | 206/372 |
| 5,979,634 A | | 11/1999 | Odegard et al. | |
| 6,312,260 B1 | * | 11/2001 | Kumar et al. | 206/368 |
| 6,382,575 B1 | * | 5/2002 | Frush et al. | 211/85.13 |
| 6,561,805 B2 | * | 5/2003 | Kumar | 206/368 |
| 2001/0042696 A1 | * | 11/2001 | Fellinger | 206/390 |

FOREIGN PATENT DOCUMENTS

CN  2192296 Y  3/1995

(Continued)

*Primary Examiner*—Bryon P Gehman
(74) *Attorney, Agent, or Firm*—Woodcock Washburn LLP (57) ABSTRACT

The invention relates to a container (100) which has a carrier (1) for the storage and presentation of surgical auxiliary material (80), in particular screws, such as bone screws, in the holding or mounting position, and at least one removable cover (48) for preventing the loss of the auxiliary material, the surgical auxiliary material (80) being presentable in isolated form. According to the invention, it is envisaged that at least two containers (100) be separably connected to one another via the cover (48) and/or the carrier (1).

17 Claims, 6 Drawing Sheets

FOREIGN PATENT DOCUMENTS

| | | |
|---|---|---|
| DE | 4122045 A1 | 1/1993 |
| DE | 29705944 U1 | 5/1997 |
| JP | 6321268 A | 11/1994 |
| JP | 2000262616 A | 9/2000 |
| JP | 2002153489 A | 5/2002 |

\* cited by examiner

CONTAINER AND CARRIER SYSTEM FOR SURGICAL AUXILIARY MATERIAL

FIELD OF THE INVENTION

The invention relates to a container and a carrier system for surgical auxiliary material.

BACKGROUND OF THE INVENTION

The prior art discloses storage, transport and presentation systems for surgical auxiliary materials, such as screws, nails and pins, which are available to a surgeon during an operation together with implants.

The implants and the auxiliary materials for fixing the implants in and on the patient must be sterilized and should be capable of being stored in a sterile condition for as long as possible. In their storage position and in their containers, the auxiliary materials should also be capable of being washed without having to additionally remove them from the container for this purpose.

It is known from the patent literature, through DE-A1-41 22 045, that bone screws can be stored in sterilization containers. In this context, DE-A1-41 22 045 has proposed using a perforated plate on which a plurality of containers are positioned in a stable manner. Such a container has place for ten bone screws.

A product range of a company which operates under the company name KLS-Martin with head office in Florida, USA, is available on the specialist market. The product range includes trays having different compartments for holding surgical instruments and tools. A perforated plate which is also described in DE-A1-41 22 045 is present in one of the compartments. A large number of screws, in particular bone screws, are present directly in the perforated plate. The screws can all be held simultaneously. If such a tray slips during the day to day work in a hospital or becomes inverted, the screws can fall on to the floor.

The same supplier also offers a plastic system which likewise represents a sterilizable tray. The screw compartment consists of a multiplicity of elongated, oval insertion positions into which screw holders or carriers for screws can be inserted. Each screw holder or carrier is provided with a cover under which, in the filled state, a group of screws of the same type, as a rule of five screws of the same type, is present.

A surgeon or his surgical team is frequently under enormous physical stress during complicated operations. Each manipulation should be capable of being carried out precisely. Particularly with small auxiliary materials which are required for fixing the implants, surgeons have problems since their hands are frequently larger than, for example, the screws which are to be used on the patient and which are to fix the implants to the bones underneath.

As a rule, the surgeon would always like to be able to pick up with his tool only that screw which he actually needs at the particular moment. All the remaining auxiliary material should be capable of remaining secured until it is required. In the secured state, it should also be permitted to be exposed to slight vibration without losing its sterile property by, for example, falling onto the floor. This is because as soon as something falls on to the floor it is as a rule unsterile even in the secured state. Preferably, the carriers should therefore not be permitted to leave the tray unintentionally.

In preparation for an operation, appropriate carrier systems can be assembled. Particularly in the case of emergency operations, only a very short time is available for assembly. To permit fast assembly, carrier systems should be capable of being equipped easily in the correct quantities and, after equipping it should be capable of withstanding the rough day to day work in a hospital without the tray being able to fall to the floor. At the same time, the requirement that the auxiliary material be easily accessible or removable and optionally be capable of being resterilized during a preparation, which is apparently contrary to the above, must not be neglected.

SUMMARY OF THE INVENTION

The container has a carrier for the storage and presentation of surgical auxiliary material, in particular screws, such as bone screws, in the holding or mounting position and at least one removable cover to prevent loss of the auxiliary material. The surgical auxiliary material can be presented in isolated form. According to the invention, at least two such containers are separably connected to one another via the cover and/or via the carrier.

The term "can be presented in isolated form" is understood herein as meaning that the auxiliary material can be offered individually to the surgeon. This is in contrast to loose auxiliary material as contained, for example, in a box. The screws are contained therein without sorting and in random distribution. However, screws which can be presented in isolated form are already isolated prior to presentation to the surgeon, i.e. detached from the loose group in which the auxiliary material is usually delivered, and organized. Preferably, the auxiliary material not only can be presented in isolated form but can even be presented individually. This means that only an individual or single auxiliary material, i.e. only one piece of auxiliary material per container, is offered in each container.

A working example of the invention envisages that the surgical auxiliary material can be presented in isolated form by virtue of the fact that the carrier has only one holding position for holding a single auxiliary material. Another embodiment envisages the auxiliary material being presented in isolated form by virtue of the fact that a removable cover is provided for each individual holding position. The presentability in isolated form is consequently firstly ensured by the fact that only a single auxiliary material can be held in each carrier. For this purpose, each carrier has only a single receptacle. Presentation of the auxiliary material in isolated form and individually consequently coincide in this embodiment. Secondly, the presentability in isolated form is, however, ensured by virtue of the fact that each individual piece of auxiliary material is covered by a single cover. Thus, a plurality of auxiliary materials may also be present in a container and of course offered in isolated form. For this purpose, the carrier may have a plurality of holding positions in which in each case an auxiliary material can be held. These are covered by one cover in each case.

The term "separably connected" is understood herein as meaning that the containers are initially connected to one another. However, this connection can be undone by the surgeon. The containers are therefore separable. One embodiment in this context envisages that at least two containers be separably connected via the covers thereof. According to a further embodiment, at least two containers are separably connected via the carriers thereof.

The connection is preferably effected during the manufacture of the containers. For example, a plurality of carriers or a plurality of covers can be connected to one another, i.e. can be manufactured in one piece. The connection between the carriers or the covers is, however, comparatively weak so that individual carriers or covers can be broken off, with the result that they are separated. A predetermined breaking point is preferably provided. According to another variant, the separable connection is effected by means of a stopper on one element and a corresponding orifice on the other element.

A further embodiment of a container once again has a carrier for the storage and presentation of surgical auxiliary material, in particular screws, such as bone screws, in the holding or mounting position, and at least one removable cover for preventing loss of the auxiliary material. According to the invention, the surgical auxiliary material can be presented in isolated form by virtue of the fact that at least two containers for an individual auxiliary material each are separably connected to one another via the cover and/or via the carrier. According to the invention, the surgical auxiliary material can alternatively be presented in isolated form by virtue of the fact that a separate removable cover is provided for each individual holding position for holding a single auxiliary material in a container in which a plurality of auxiliary materials can be held, the individual covers being separably connected to one another.

A carrier for surgical auxiliary material, such as pins, nails, but especially screws, such as bone screws, has in particular a storage area and at least one leg or at least two legs. The carrier has the form of a table whose storage support area, i.e. the upward-facing surface on the storage area, is intended for carrying a surgical screw or a pair of screws or the like. The legs project substantially at right angles out of the side opposite the storage support area. A carrier is designed so that it can receive only an isolated auxiliary material, in particular an isolated screw or isolated pair of screws, in a holder so that the head of the auxiliary material or the head of the screw rests on the storage support area and the shaft thereof is inserted between the legs or parallel to the legs.

The storage area is in particular provided with at least one recessed area which can also be designated as a recess or cut-out and is dimensioned so that a matching tooth of the cover can slide over the recessed area onto the side opposite the storage support area. This results in anchoring of the cover on the carrier.

The carrier is formed by its features according to the invention so that it can advantageously isolate surgical auxiliary material. Each individual auxiliary material is consequently held separately in the corresponding individual or isolatable receptacle. Preferably, each carrier can hold and store only one (or a few, in particular two or a pair) of the auxiliary materials altogether. Owing to the position of the centre of gravity and the shielding of the legs and of the storage area, the auxiliary material fits securely in and on the carrier under the usual circumstances. Virtually the entire surface of the auxiliary material is freely accessible and can thus be sterilized, except where the carrier grips the screw. Here too, the screw or the auxiliary material is, however, sterile without problems because it has play there. In practice, the carriers with the screws are repeatedly washed in a washing machine and then sterilized.

The recessed areas according to the invention, which are present on the sides of the carrier, perform two functions. Firstly, the teeth of the cover can snap in under the recessed areas. If the carrier is taken between thumb and index finger, the recessed areas secondly facilitate gripping of the small object. However, during day to day work in the hospital, gripping is as a rule effected by means of forceps, so that it is particularly advantageous to offer gripping areas for the forceps by means of recessed areas.

The legs of the carrier open into runners which can also be designated as locking rails. These have a rounded shape overall and point laterally outwards. In an alternative embodiment (depending on the formation of the sliding rails), the legs can also point inwards. Where at least two legs are present, the runners improve the ability of the carrier to stand when the runners are longer than the screws. In the cases where the carriers are shorter than the screws, the runners perform another function together with the carrier system. If the carriers are connected to a carrier system, the carriers snap according to the invention into said system by means of the runners.

According to a further preferred embodiment, the legs of the carrier have at least one projection each as a stop lug, which is spring-mounted. Thus, a tab by which the projection is surrounded is formed in the leg. The projection is spring-mounted therein. Alternatively, the projection can also be formed integrally with the leg or can be mounted on the leg and the leg itself can be springy. In each case, it is envisaged that the carrier is capable of snapping into a carrier system with the aid of this projection.

The holder is an orifice or a hole having a diameter which is greater than the shaft and less than the head of the auxiliary material to be held, in particular the screw. The screw can sink between the legs of the carrier until the head of the screw rests on the storage support area.

The corners of the storage area are rounded. Points and sharp edges are avoided; thus, the danger of injury, in particular of surgical gloves or the like, is reduced.

The legs provide extensive stop sections on which a plurality of carriers can be arranged one behind the other in series, which carriers mutually stabilise one another and group together. According to a particular development, however, the carriers are in particular also integrally connected or injection moulded with adjacent carriers via thin burrs and can be isolated by means of force.

For sterilization, the carrier is made of a sterilizable plastic. This is chosen so that sterilization by means of ionizing radiation, gas and optionally steam is possible.

The cover is a preferably curved cover having at least one tooth which stretches across the storage support area from one short side to a second short side of the storage area. This tooth may also be designated as projection. The curvature of the cover offers a cavity at least the size of the head of the screw being held. The curvature follows, for example, a radius which forms virtually a semi-circle. Furthermore, the cover has preferably been produced from a transparent, sterilizable plastic.

The cover of the carrier has, in the region of the highest elevation of the curvature, a handle which is preferably equipped with four sides which are optionally formed so as to be easy to grip, and point in a direction opposite to that of the screw to be held. Two sides, in each case facing a tooth, have borders. According to a particular development, a stopper projects from one side. An orifice is provided on another side. Stopper and orifice form a plug connection system.

In an alternative embodiment, it is also intended to use a predetermined breaking system instead of the plug connection system comprising stopper and orifice—as already indicated above. The plug connection system is produced from a material which can break at its transition points, which are comparable to the stopper and orifice system.

Such a carrier with or without lid forms the container according to the invention. This can co-operate with a carrier system. Various carrier systems are conceivable. A carrier system according to the invention has an extended tray-like form which is provided at regular intervals with sliding rails whose sliding surfaces are present on the undersides and which are all parallel to one another, in particular equidistant.

According to a further development, stop lugs which are present between the sliding rails at the edges of the carrier system are furthermore provided in such a carrier system. Such carrier systems together with carriers according to the invention are therefore designed to snap in carriers between the sliding rails by a vertical downward movement. The snapped-in carriers are displaceable in the carrier system in a horizontal direction on the sliding rails. When the carriers are equipped with screws, they are retained by the stop lug on the carrier system. However, if the screw is removed from the carrier, the surgeon or his assistant can easily remove the carrier from the carrier system laterally along the course of the rail. The empty carrier can be pushed over the stop lug while the still equipped carriers are automatically retained.

According to the invention, alternative retaining systems are formed if nubs or constrictions in the region of the sliding rail permit lateral removal of a carrier only after application of force against a locking or frictional resistance. In these systems, carriers with or without auxiliary material can be removed.

In order to use a fully equipped system, the surgeon removes the separably connected covers as a whole. All auxiliary materials secured by this cover are thus accessible. Alternatively, it is intended that he grips the handle of a cover and releases from the locking by the teeth in the recessed areas the number of covers corresponding to the auxiliary materials he requires at the time. The other auxiliary materials remain closed or secured by means of a cover.

Another, simpler carrier system according to the invention can hold substantially fewer carriers. This carrier system comprises a U-shaped base having a cavity between the extremities recessed inwards, the ends of U-shape. Their uppermost surfaces serve as a carriage for the underside of the storage support area of a carrier. Such a system, too, can be very well sterilized. It is more compact and therefore easier to specify and to assemble than the carrier system first described. For removal, the surgeon can both remove the covers as a whole and move the covers on the slide and thus gain access to only individual auxiliary materials.

Instead of the cohesive covers mentioned, flap-like covers are also included by the invention, which covers do not so much provide complete covering but ensure prevention of loss by being capable of swivelling away laterally. These flaps may be hinged to the carrier or may be formed integrally with it (by injection moulding). They can be provided within the scope of the invention for individual carriers having individual receptacles or for carriers having a plurality of receptacles. Such a system would be inventive even independently of the other information in this Application. It could, for example, replace the removable lids of said systems from KLS Martin. The advantage of such flaps which can be swivelled away is that they always remain on the carrier and the manipulation is therefore easier in certain circumstances than with lids which are completely removable. Another alternative would be sliding lids.

The list of reference numerals in the drawing, together with the subjects described or protected in the Claims, is an integral part of the disclosure of this Application.

BRIEF DESCRIPTION OF THE DRAWINGS

The invention can be even better understood by referring to the attached exemplary figures. They are described in relation to one another and as a whole. Identical reference numerals denote identical components, and reference numerals with apostrophes indicate functionally identical components.

DETAILED DESCRIPTION OF THE PREFERRED EMBODIMENTS

Figure 1:
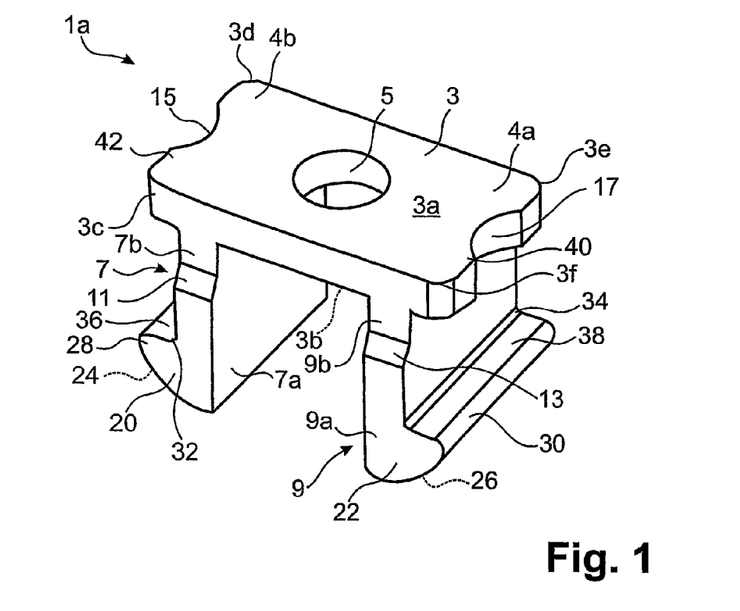
FIG. 1 shows a first embodiment of a carrier according to the invention.

FIG. 1 illustrates a carrier 1 for a surgical screw which is suitable for holding, storing and presenting a surgical screw in isolation in the sterile state. The carrier 1 comprises a storage area 3 on whose two outer end regions 4a, 4b a distance apart from one another in each case a leg 7, 9 is present. Each leg extends in each case on the side 3b which is opposite the storage support area 3a and is also referred to as underside, starting at almost a right angle to the direction of the storage area 3. The first leg 7 has an upper region 7b and a lower region 7a, and the second leg 9 has a lower region 9a and an upper region 9b. In the lower region 7a of the first leg 7 and in the lower region 9a of the second leg 9, the respective leg opens into a runner 20, 22. The first runner 20 is the runner for the first leg 7, and the second runner 22 is the runner for the second leg 9.

The legs 7, 9 are designed similarly to one another in shape and, in their upper regions 7b, 9b, have approximately the same thickness as the thickness of the storage area 3. Only in the lower region 7a, 9a do the legs 7, 9 differ in their thickness, in order to form the runners 20, 22. The runners 20, 22 have undersides 24, 26 which as a whole are rounded and approximately form a quadrant which, in the rounded transition regions 28, 30, becomes the surfaces 36, 38. The runners 20, 22 run along the legs 7, 9 and are parallel to the short sides 40, 42 of the storage area 3. The runners 7, 9 have further rounded areas 30, 34 which are inclined in opposite directions convex to the transition regions 28, 30.

Most corners and edges of the carrier are rounded, for example the corners 3c, 3d, 3e, 3f, which bound the storage support area 3a. As a result, the carrier 1 presents less danger of injury for the finger or surgical glove of a surgeon and the wound of a patient. By means of the bevels 11, 13, the legs 7, 9 form projecting sections to the lower regions, i.e. where the runners 20, 22 are formed. Below and above the bevels, the legs 7, 9 are extensive.

The storage area 3 is provided with a hole 5 which can be arranged as a cut-out in the centre of the storage area 3. The hole 5 is preferably arranged centrally, i.e. has the same distance from all edges of the same type of the storage area 3. In a variant not shown, it is of course also conceivable for the hole to be arranged eccentrically. The hole 5 is intended to hold an auxiliary material. Auxiliary material is to be understood as meaning screws, pins, rivets or the like. However, the invention is not limited thereto. Thus, this term may also include drills, cutters or other tools. For example, in the case of a surgical screw, the hole encloses the screw thread thereof partly and encircles it. At the same time, it is so small that the screw head of the surgical screw cannot slip through. Each carrier is preferably equipped with only one hole 5.

The carrier may have different colours in order to indicate to a surgeon, for example, which auxiliary materials are stored by them. Accordingly, the holes too may have different sizes.

However, it is also possible to provide a plurality of holes, in particular two holes 5. In the preferred working example shown, only one hole 5 is provided.

The sides 40, 42 of the storage area 3 have recessed areas 15, 17 which are positioned approximately at half the length of the short sides 40, 42. The recessed areas 15, 17 have dimensions such that teeth 44, 46, which project integrally from a cover 48 according to FIG. 2A and FIG. 2B, can engage the recessed areas in order to anchor the cover 48 to the side 3*b* opposite the storage support area 3*a*.

As is evident from FIG. 2, the cover 48 has an arched shape which can encompass the head of a surgical screw and protect it from perpendicular contact. A handle 50 which projects from the cover and has four sides 50*a*, 50*b*, 50*c*, 50*d*, pairs of which may have the same dimensions, is present in a region above a fictitious mid-point of the cover 48, which mid-point is outside the encompassed circular section of the curvature.

Figure 3:
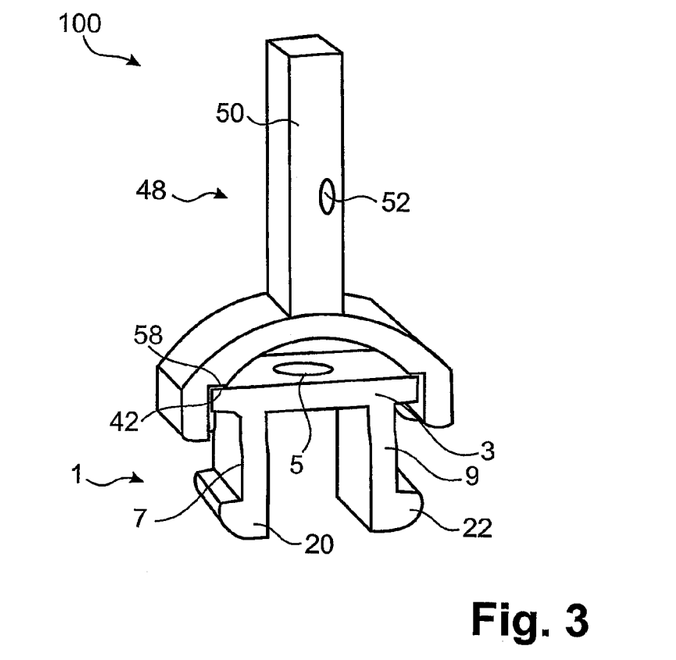
FIG. 3 shows the interaction of the carrier according to FIG. 1 with a cover according to FIG. 1 (A)

FIG. 3 illustrates the interaction of the carrier 1 with the cover 48. Carrier 1 and cover 48 form a complete container 100. The teeth 44, 46 are engaged. The stopper 52 which projects from the side 50*a* of the handle 50 performs the task of forming a fastening for a second cover so that one side of a handle of the second cover is parallel to the side 50*a* of the first handle 50 in large parts and together forms a larger handle which consists of the handles 50, 50*a*. The situation after coupling of a plurality of containers 100 is clearly evident from the diagram in FIG. 4. Coordinated with the stopper 52 is a corresponding orifice 54 on the opposite side 50*d* of each handle 50. The connection of a plurality of containers is accordingly effected with the aid of the stoppers 52 and the corresponding orifices 54. The carriers are consequently connected to other carriers via the covers. This has the advantage that filled containers can be connected via the cover to form a plurality of containers, which facilitates their handling. However, once the cover 48 has been removed for removing the auxiliary material, the empty carrier 1 can now be separated individually from the other carriers.

As mentioned above, a further preferred working example of the invention envisages a predetermined breaking point between the covers or the carriers. The unit comprising covers or carriers is produced in one piece, for example by injection moulding. A weak connection, which is present, for example, only at one point, is thus created between the individual elements of the unit. Thus, the stopper 52 in FIGS. 3 and 4 may also be regarded as this weak connection, i.e. as a predetermined breaking point. In the connected state, the covers are connected to one another by means of this. However, the surgeon separates the cover by separating at the predetermined breaking point.

The cover 48 is provided on its insides with support areas 58 which can support the cover 48 with the associated end regions 4*a*, 4*b* of the carrier 1. In their middle, the teeth 44, 46 project. The container 100 is formed when the cover 48 firmly engages the carrier 1 in the region of the recessed areas 15, 17 on the short sides 40, 42 by means of the teeth 44, 46, and the cover 48 rests on its support areas 58. It is important for sterilization that the surgical screw continues to be readily accessible in spite of the cover so that sterilizing steam can enter and exit.

Figure 4:
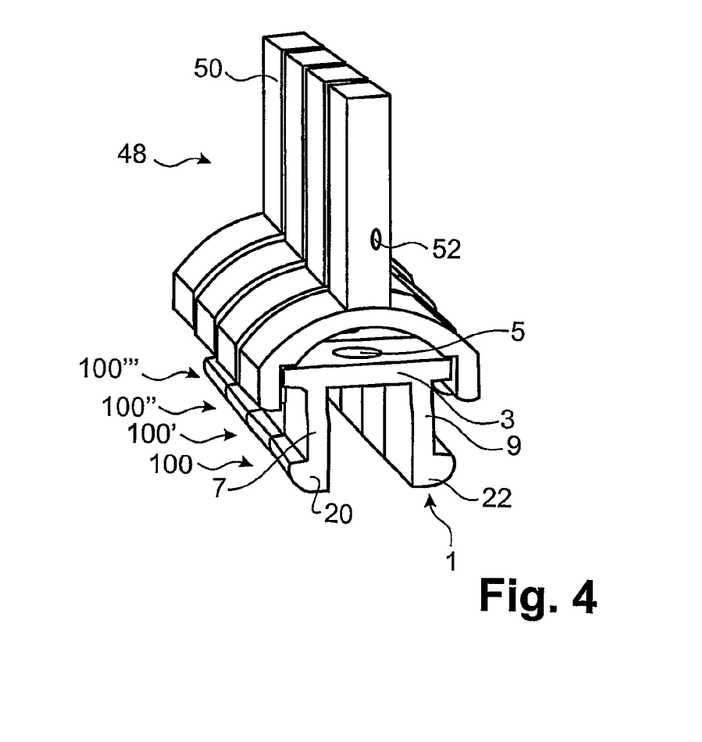
FIG. 4 shows the interaction of a plurality of carriers of the type according to FIG. 3.

This plug connection system comprising stopper 52 and orifice 54 provides a plug connection system as shown in FIG. 4 for numerous surgical screws which are protected in each case from perpendicular contact. However, these screws are present in isolated form and securely per carrier 1 in each container 100, 100', 100'', 100'''.

Figure 2A:
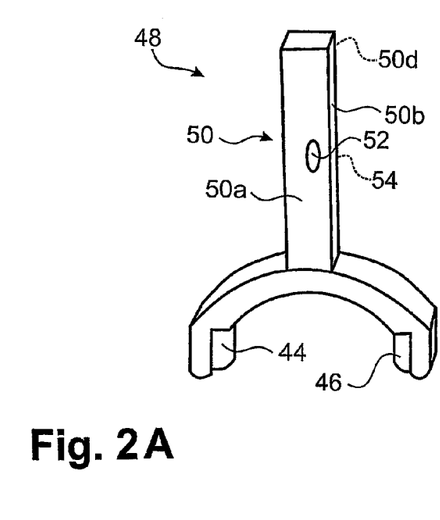
FIG. 2A shows a first embodiment of a cover in vertical view.
Figure 2B:
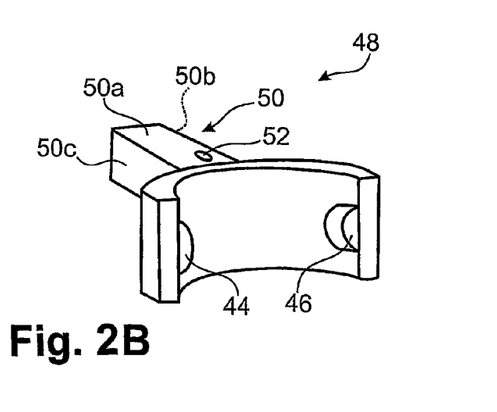
FIG. 2B shows the first embodiment of the cover in horizontal view.
Figure 5:
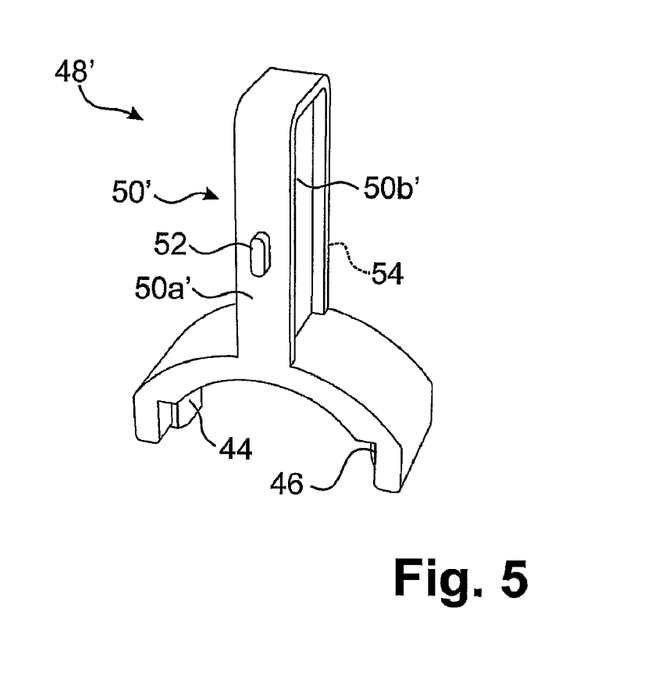
FIG. 5 shows a further cover according to the invention for a carrier according to FIG. 1, but having other proportions.

FIG. 5 shows a further cover 48' according to the invention, which is largely similar to a cover according to FIG. 2A or FIG. 2B. The cover 48' has two teeth 44, 46, a first tooth 44 and a second tooth 46, which are designed so that they fit together with corresponding recessed areas 15, 17, as shown, for example, in FIG. 1, and can snap in. The handle 50' of the cover 48' has a shape different to that of the handle 50 according to FIG. 2A. In FIG. 5, the two sides 50*a*' and 50*b*' of the handle 50' can be seen. The side 50*b*' has a border. The border has the effect that the fingers of a user can better grip the handle 50'. For further improvement of the grippability of the handle 50', the surface may be ribbed or provided with hubs or the like. The side 50*a*' and the side opposite this side may furthermore be labelled or coded—for example with a machine-readable code. It is also possible to label the carrier area 3, for example with length data of the screws.

Figure 6:
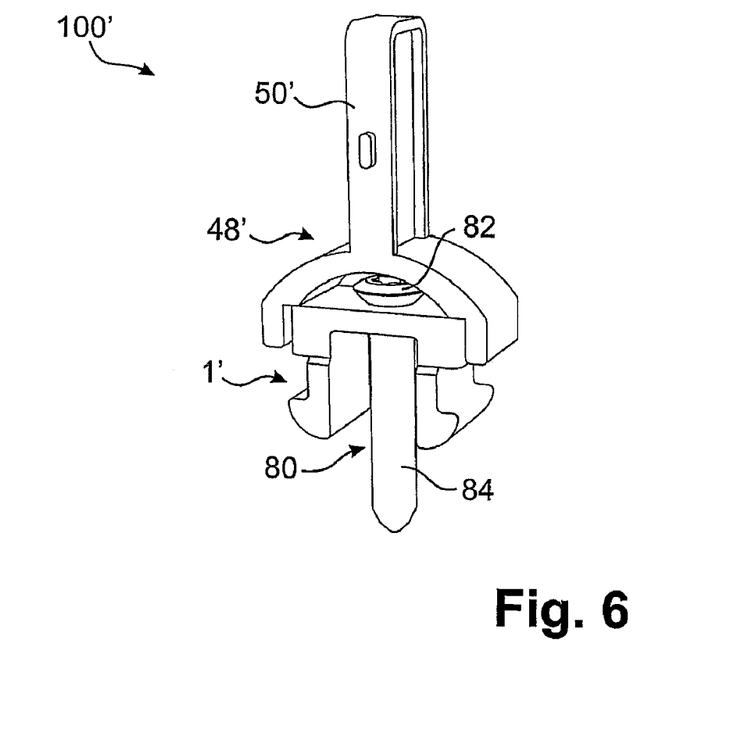
FIG. 6 shows a carrier according to FIG. 1 having a cover according to FIG. 5 which has received a surgical screw.

FIG. 6 shows a cover 48' with handle 50' of a carrier 1' which carries a surgical auxiliary material, such as screw 18 shown schematically. The screw 80 comprises screw head 82 and a screw shaft 84 which hangs loosely in the hole.

Figure 7:
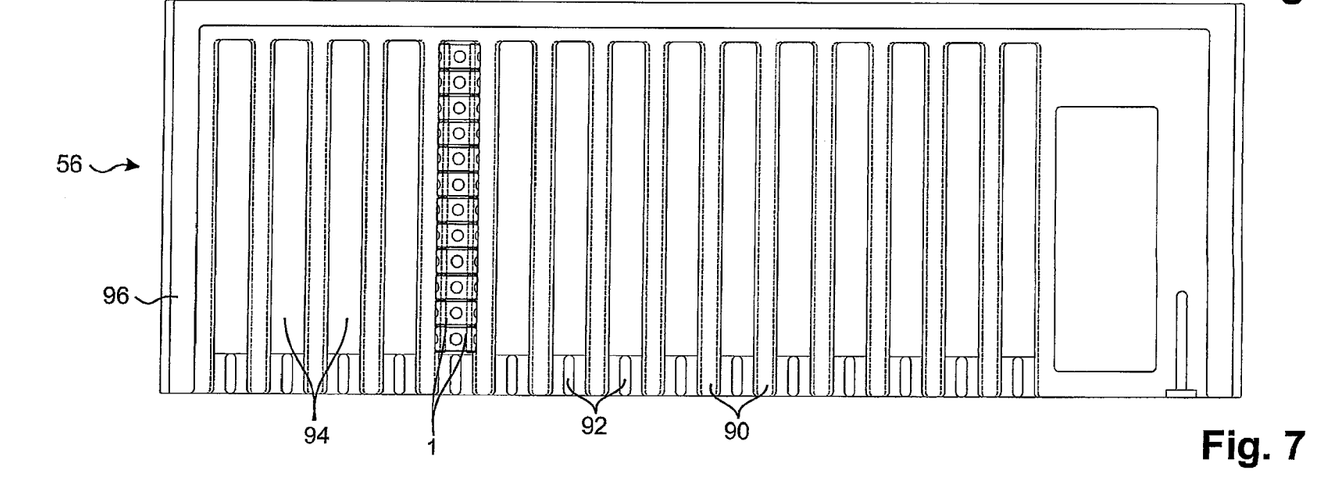
FIG. 7 shows a carrier system having individual carriers according to FIG. 1, in plan view.
Figure 8:
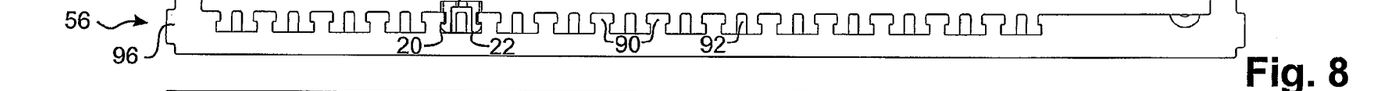
FIG. 8 shows a first embodiment of a carrier system according to FIG. 7 from a front view.

FIG. 7 shows a carrier system 56 according to the invention, in plan view. This is shown in FIG. 8 in cross-section and in FIG. 10 in perspective view. Fig. shows a section through the (further) carrier system 56'. The carrier system 56, 56' is equipped with sliding rails 90, 90' which are a distance apart across a free space 94. The free space has dimensions such that carrier 1 can engage between the sliding rails 90, 90'. In each case a stop lug 92 is provided at an end of each free space 94. The carriers 1 are present in the normal storage state in the region of the free space 94 which begins behind the stop lugs 92. The carrier system 56, 56' has a border 96, 96' running around three sides.

Figure 9:
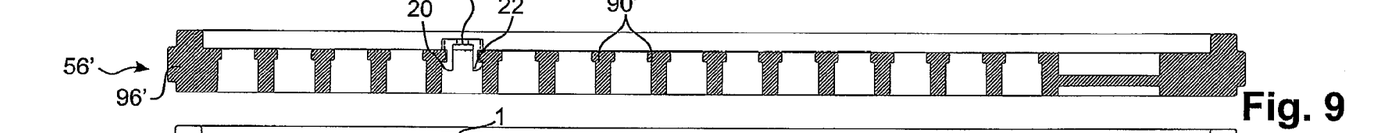
FIG. 9 shows a second embodiment of a carrier system according to FIG. 7 from a front view in section.
Figure 10:
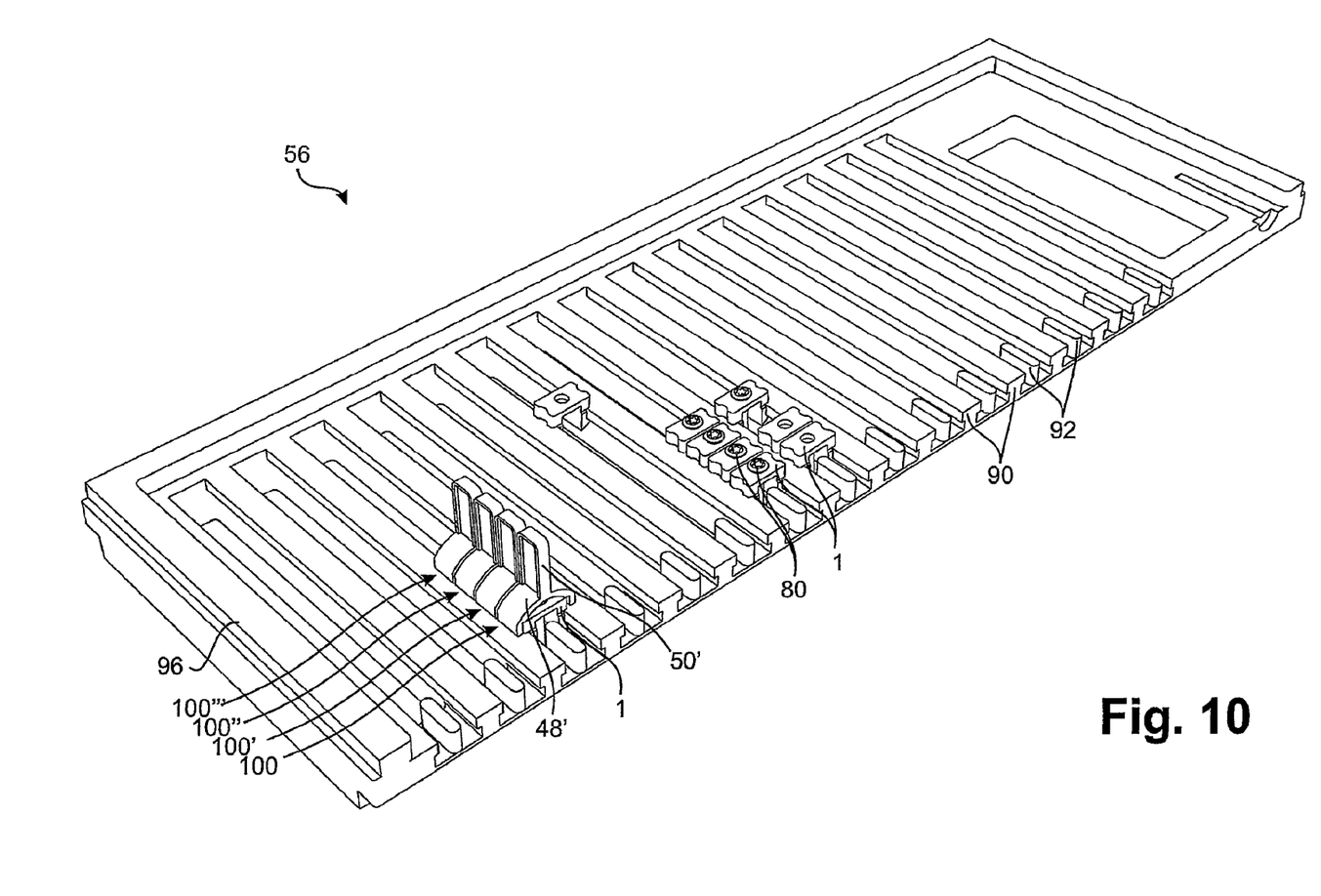
FIG. 10 shows a carrier system according to FIG. 7 from a perspective view.

The two developments of FIGS. 7, 8 and 10 on the one hand and of FIG. 9 on the other hand differ, inter alia, in that the sliding rails 90, 90' have different heights. In the cases where carriers are to be prepared with long screws 80, a carrier system 56 having higher sliding rails 90' should be chosen, whereas in cases where only short screws 80 are used, a carrier system 56 having shorter sliding rails 90 should be used. It is also conceivable to have a modified carrier system 56 which has a certain number of high sliding rails 90' and a certain number of short sliding rails 90—in each case for holding different carriers or carriers having different auxiliary materials.

The carrier systems 56, 56' are thus provided with a protective frame 96, 96' such that the frame is higher than the extent to which the storage support area 3*a* of the carriers 1 projects upwards. The runners 20, 22 grip laterally under the sliding rails 90, 90' and thus ensure a displaceable, snap-in mechanism so that, after snapping in, the carriers cannot be removed in the vertical direction away from the carrier system but are displaceable in a horizontal direction parallel to the sliding rails 90, 90'.

FIG. 10 shows the carrier system 56 from FIG. 7 in a perspective view. The carrier system 56 carries various carriers 1, some of which are empty, some of which have covers 48' and some of which are provided with screws 80. The stop lugs 92 retain the carriers 1 which are equipped with screws 80 because they block the free horizontal path from the carrier system 56 by virtue of the screws striking the stop lugs 92. The covers 48 with their handles 50 allow the isolated screws 80 to slip back and forth easily in that, for example, a surgeon only has to reach for a cover and a total prepared group of a plurality of containers 100, 100', 100", 100''' can then move along the sliding rails 90, 90' by means of the system comprising stopper and orifice.

Figure 11:
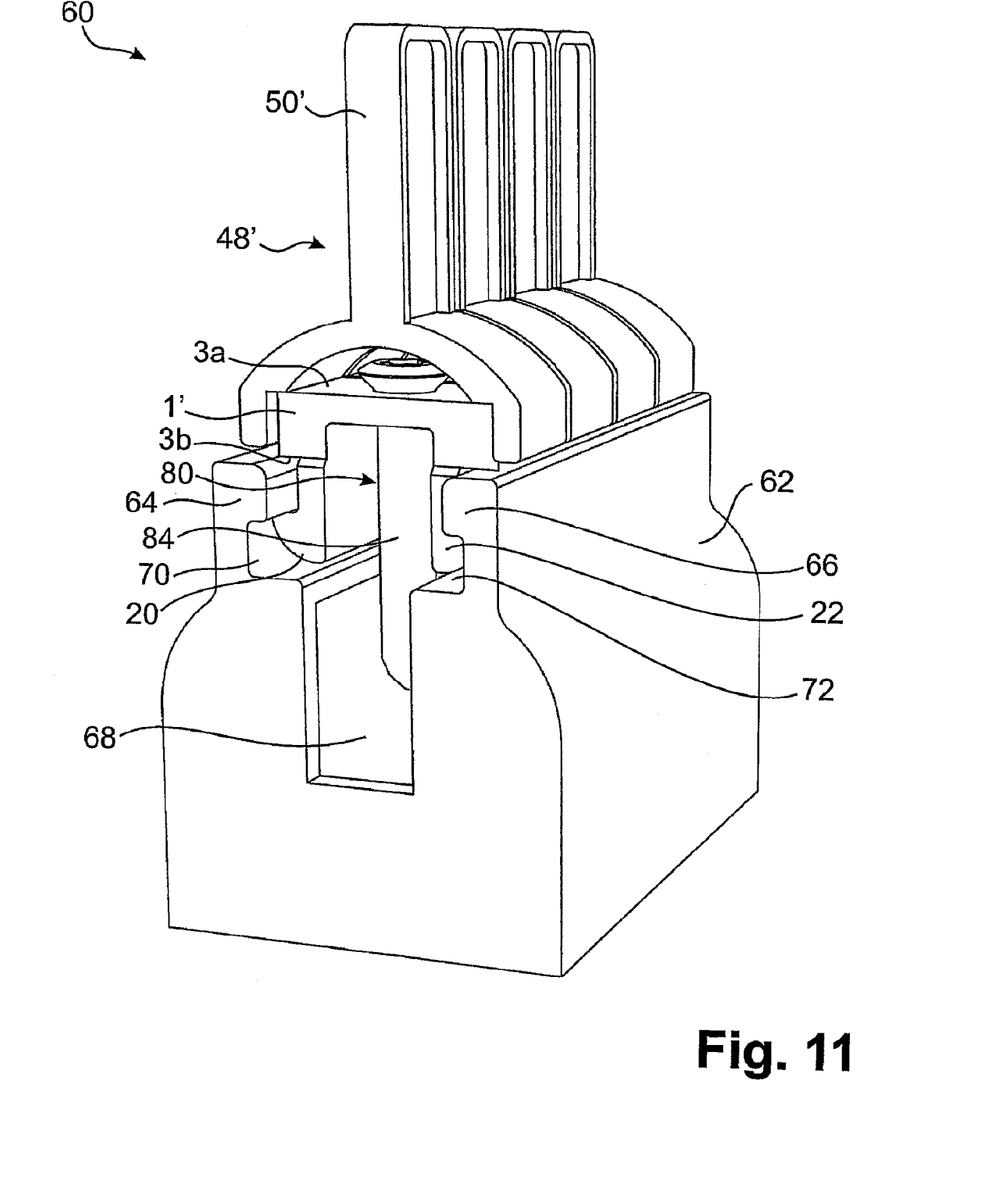
FIG. 11 shows a carrier system according to a third embodiment which is more compact than the carrier system according to FIG. 7.

FIG. 11 discloses a possible retaining body 60 which consists of a carriage 62 and at least one carrier 1' and one cover 48'. The carriage 62 has the form of a clamp or the form of a customary clip which forms a U-piece and, at its extremities 64, 66, touches and holds the side 3b of the carrier 1', which side is opposite the storage support area 3a. The cavity 68 of the U-piece is tailored in its height and width to the carrier 1 so that a screw 80 can be held in the cavity 68. Notches 70, 72 which ensure the stability of the carriage 62 and at the same time provide space so that the runners 20, 22 can slide in the notches are present on the insides of the extremities 64, 66.

A further alternative embodiment of a carrier envisages that it has only one leg or differently designed legs. Thus, one leg may be formed as such and can be supported, for example, in the carrier system. The other "leg" is designed as an engaging element which engages under the sliding rail and snaps into the carrier system. Such a carrier can be more easily removed or unclipped from the sliding rails in an upward direction—i.e. in the direction opposite to the insertion direction.

The carriers are made of sterilizable plastic and can be colour-coded. On the basis of the colour code, the surgeon can recognise which screw he has before him. It is particularly advantageous if the carrier bears an easily recognisable colour code, such as, for example, complete colouring, while the cover is produced from transparent plastic. The transparent plastic enables the user, e.g. the surgeon, to easily cast a glance over the covered screw and to once again ascertain whether the auxiliary material for his operation, which he expects to find there, is actually also present underneath the cover. Because the carriers and the carrier system can be produced by plastic injection moulding, the system can be produced very economically.

LIST OF REFERENCE NUMERALS

1—Carrier
3—Storage area
3a—Storage support area
3b—Opposite side
3c—First corner
3d—Second corner
3e—Third corner
3f—Fourth corner
4a—First end region
4b—Second end region
5—Hole
7—First leg
7a—Lower region
7b—Upper region
9—Second leg
9a—Lower region
9b—Upper region
11—Bevel
13—Bevel
15—Recessed area
17—Recessed area
20—First runner
22—Second runner
24—First underside
26—Second underside
28—First transition region
30—Second transition region
32—First rounded area
34—Second rounded area
36—First surface
38—Second surface
40—First short side
42—Second short side
44—First tooth
46—Second tooth
48—Cover
50—Handle
50a—First side of the handle
50b—Second side of the handle
50c—Third side of the handle
50d—Fourth side of the handle
52—Stopper
54—Orifice
56—Carrier system
58—Support area
60—Retaining body
62—Carriage
64—First extremity
66—Second extremity
68—Cavity
70—First notch
72—Second notch
80—Screw
82—Screw head
84—Screw shaft
90—Sliding rail
92—Stop lug
94—Free space
96—Protective frame
100—Container

The invention claimed is:

1. A sterilization container for retaining a surgical auxiliary material, the sterilization container comprising:
   a carrier having a storage area at an upper end, the storage area defining an upper surface that retains a surgical auxiliary material such that the surgical auxiliary material is accessible to an ambient environment outside the carrier, wherein the storage area defines a hole that receives the surgical auxiliary material such that the surgical auxiliary material extends through the storage area, and the carrier further comprises legs extending downward from the storage area, the legs configured to engage a carrier system; and
   a cover removably attached to the storage area of the carrier such that a portion of the surgical auxiliary material is disposed between the cover and the upper surface of the storage area.

2. The container of claim 1, wherein the cover further comprises an upwardly-extending handle.

3. The container of claim 1, wherein the surgical auxiliary material is a bone screw.

4. The container of claim 1, wherein the surgical auxiliary material has a head portion configured to lie at least partially above the hole, and a shaft portion configured to lie at least partially below the hole.

5. The container of claim 1, wherein the cover has inwardly-extending elements for engaging the storage area of the carrier.

6. The container of claim 5, wherein the inwardly-extending elements are teeth.

7. The container of claim 1, wherein the at least one of the legs has a portion that extends substantially transverse from the storage area.

8. The container of claim 1, wherein at least one of the legs has a runner.

9. The container of claim 1, wherein at least one of the legs is configured to engage a rail of the carrier system.

10. The container of claim 1, wherein the container is configured to be placed next to another container in the carrier system.

11. A sterilization carrier system comprising:
at least first and second rails;
at least first and second carriers disposed along the first and second rails, wherein each of the first and second carriers includes a storage area that defines a hole extending therethrough, and the holes are each configured to receive a surgical auxiliary material; and
first and second removable covers attached to the first and second carriers, respectively, so as to cover the holes of the first and second carriers, respectively.

12. The carrier system of claim 11, wherein the first carrier has at least one leg configured to be disposed between the first and second rails.

13. The carrier system of claim 11, wherein the first carrier is slidably disposed along the first and second rails.

14. The carrier system of claim 11, wherein the first carrier is retained by the first and second rails.

15. The carrier system of claim 11, further comprising a channel disposed between the first and second rails, wherein the channel is configured for the surgical auxiliary material to extend therein.

16. The carrier system of claim 11, wherein the surgical auxiliary material is a bone screw.

17. The carrier system of claim 11, wherein the first removable cover is removable from the first carrier independent of the second removable cover.

* * * * *